United States Patent [19]

Harrison

[11] Patent Number: 4,496,904
[45] Date of Patent: Jan. 29, 1985

[54] EDDY CURRENT MEASUREMENT APPARATUS FOR NON-DESTRUCTIVE TESTING IN THE VICINITY OF A FASTENER

[75] Inventor: David J. Harrison, Farnham, England

[73] Assignee: The Secretary of State for Defence in her Britannic Majesty's Government of The United Kingdom of Great Britain and Northern Ireland, London, England

[21] Appl. No.: 336,341
[22] PCT Filed: May 19, 1981
[86] PCT No.: PCT/GB81/00089
  § 371 Date: Dec. 31, 1981
  § 102(e) Date: Dec. 31, 1981
[87] PCT Pub. No.: WO81/03381
  PCT Pub. Date: Nov. 26, 1981

[30] Foreign Application Priority Data

May 22, 1980 [GB] United Kingdom ............... 8016887

[51] Int. Cl.³ .................. G01N 27/72; G01R 33/00; G01N 27/82
[52] U.S. Cl. .................. 324/227; 324/238; 324/262
[58] Field of Search .................. 324/225–227, 324/238, 240, 241, 242, 243, 262, 237

[56] References Cited

U.S. PATENT DOCUMENTS 4,322,683 3/1982 Vieira et al. .................. 324/225
4,326,166 4/1982 Pigeon et al. .................. 324/225

Primary Examiner—Gerard R. Strecker
Assistant Examiner—Walter E. Snow
Attorney, Agent, or Firm—Cushman, Darby & Cushman

[57] ABSTRACT

Measurement apparatus receives a signal from an eddy current transducer (20) excited by a generator (24). A signal generator (21) generates a signal at a predeterminable reference level which is combined with the transducer signal to produce a measurable signal at output (23). The output of the signal generator (12) is determined by a set balance control (15) which may be set by amplitude controls (29,30) in accordance with control coefficients applied via data bus 43. The output of the signal generator (21) may be predetermined iteratively in a calibration phase preceeding measurement. The present invention overcomes the problem of providing an inactive matched eddy current transducer to balance the signal provided by the measurement transducer (20). A second transducer (49) may be switched (50) to replace the signal generator (21) to enable positioning of the measurement transducer (20) with respect to a workpiece.

2 Claims, 3 Drawing Figures

EDDY CURRENT MEASUREMENT APPARATUS FOR NON-DESTRUCTIVE TESTING IN THE VICINITY OF A FASTENER

This invention relates to measurement apparatus and in particular to apparatus for the non-destructive testing of engineering materials and structures by eddy current measurement.

Eddy currents may be induced in conductive materials be setting up a varying magnetic field in the vicinity of the material. Such currents give rise to a field which opposes the inducing field and may be detected by a suitable transducer. The nature and structure of the material gives rise to a characteristic eddy-current pattern. Any perturbation of the pattern indicates an area of possible defect. A field inducing transducer coil may itself be used to examine the eddy current pattern by the impedance change induced by the opposing field.

Signals due to eddy currents are small and appear superimposed on larger signals due to other effects. Typically an eddy current signal at a transducer output appears as small perturbations about a substantially constant reference level signal. In order to remove the reference level signal to give a measurable signal two transducers are arranged in a conventional bridge, so that the reference level is balanced out. Such an arrangement is described in GB Patent Application No. 2 028 510 A in which transducer coils are opposingly mounted on a common former for rotation above a rivet fastener in engineering structure. The coils are connected in a bridge to balance out the reference level signal. A defect in a fastener hole for example causes a perturbation of the eddy current pattern in that region, which is detected during rotation as a coil passes the region. The opposing coil provides a reference level signal corresponding to sound structure at a reference location and a measurable signal due to the defect is produced at the bridge output. Measurement of signal components in phase and quadrature yields information about the nature of the defect.

In bridge arrangements the transducers forming the bridge must be carefully matched. At the signal levels of interest in eddy current measurement transducers must be particularly closely matched. The accuracy to which transducers can be matched imposes a limit on the performance of a system including a bridge arrangement.

In systems which detect differences in signal level between a reference and a measurement location transducer mismatch produces a direct error and many such systems employ additional circuitry to achieve bridge balance. A fundamental limitation of such systems having bridge arranged transducers is inability to reliably detect defects at both measurement and defect locations.

According to the present invention measurement apparatus for receiving an eddy current transducer signal which varies with respect to a reference level includes a signal generator for generating a signal at substantially the reference level, the output of the signal generator being combined with the transducer signal to produce a measurable output.

Where transducers require external excitation the signal generator may take the form of means for producing a signal which is proportional to or a function of the excitation signal.

The output of the signal generator is preferably predetermined. Alternatively the output may be defined during a calibration cycle which precedes a measurement cycle, the calibration cycle advantageously involving a plurality of iterative steps. Signal generator output may be set by determining in phase and quadrature components of the reference level.

It will be appreciated that the present invention overcomes the limitations of prior art eddy current measurement since the reference level may be set to correspond to a known defect free structure or the average value of typical samples or other preferred level. Hence problems associated with mismatch and mutual defects are not encountered with measurement apparatus in accordance with the present invention.

Signal levels are preferably set by control coefficients which control for example the output of the signal generator and excitation signal. Coefficients may advantageously be computed and set by a processor in accordance with an iterative algorithm. Preferably control inputs are bus connected, with provision for additional functions such as control of a rotatable probe. Where a rotatable probe is employed opposing coils are preferably provided so that the probe may be centred iteratively by seeking symmetry during a centring cycle. One coil of a centred probe may be used in a measurement as described above.

In order that features and advantages of the present invention may be fully appreciated an embodiment of the present invention will now be described with reference to the accompanying diagrammatic drawings of which:

Figure 3:
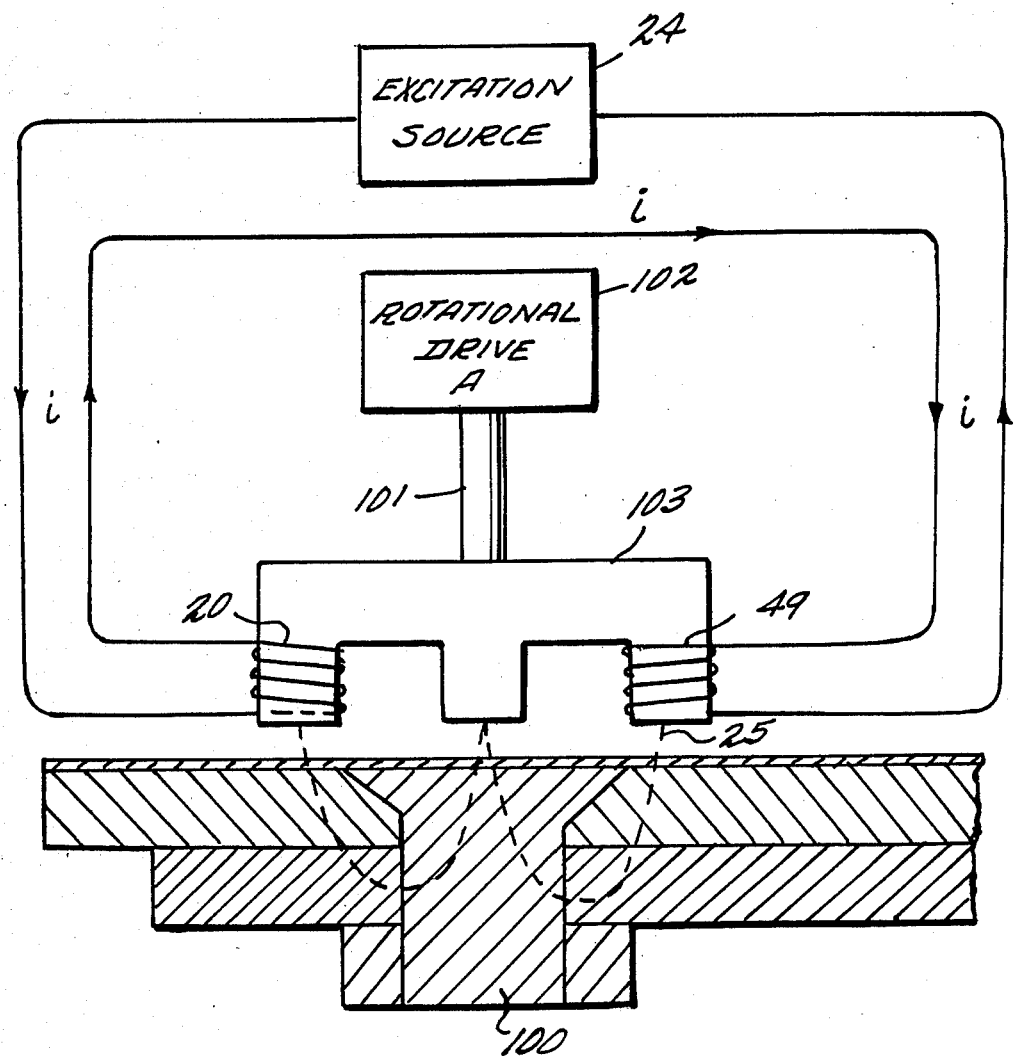
FIG. 3 represents a schematic view of a probe.

Referring to FIG. 3, the probe includes two transducers 20 and 49 which take the form of coils arranged to sense dissipated energy when placed in close proximity to an engineering material and to identify the presence of cracks by changes therein. The coils are conventionally wound on a former 103 and adapted to be rotated by a drive 102 to detect cracks or the like in a fastener 100. This results in a signal which varies with changes in dissipated energy and with respect to a reference level. In the embodiment of the probe described, two such transducers are arranged in a balanced configuration.

The transducer is supplied with sinusoidal excitation and the transducer signal varies in both amplitude and phase with respect to a reference level due to changes in dissipated energy.

The reference level may be considered to have an in phase reference level and a quadrature reference level, and in accordance with the present invention measurement apparatus includes means for generating a signal, having a component at substantially the in phase reference level and a component at substantially the quadrature reference level.

Measurement apparatus receives a transducer signal from a coil 20 which varies in both phase and amplitude with respect to reference levels and includes a balance signal generator 21 for generating a signal having in phase and quadrature components at substantially the reference levels respectively. The output of the balance signal generator is combined with the transducer signal by an amplifier 22 to produce a measurable signal, on output line 23.

An excitation signal is applied to the coil 20 by an excitation generator 24. The excitation is sinusoidal and the frequency and amplitude of the excitation signal are controlled by frequency control circuitry 25 and amplitude control circuitry 26 which applies an attenuation to the signal from the excitation generator 24. The balance signal generator 21 is arranged to produce a signal having an in phase and a quadrature component substantially at the in phase reference level and the quadrature reference level. The balance signal generator is arranged to produce a signal in phase and a signal in quadrature with the signal from the excitation generator 24 at outputs 27 and 28 respectively. These signals are attenuated by amplitude control circuitry 29 and 30 respectively and are combined by an amplifier 31 to generate a signal at output 32 having in phase and quadrature components at substantially the in phase and quadrature reference levels.

In order that the information carried by measurable signal on output line 23 may be more easily interpreted the known technique of synchronous demodulation is employed to separate the signal into an in phase and a quadrature component on signal lines 37 and 38. Demodulators 33 and 34 are driven by in phase and quadrature square wave signals on lines 35 and 36 respectively which are derived from the signal produced by the excitation generator 24.

The frequency control 25, amplitude control 26 and the amplitude controls of the in phase and quadrature components of the balance signal generator 21 are adapted to receive and may be set by a digital word received at inputs 39, 40, 41 and 42 respectively which is a control coefficient in digital format. The digital word is received from the output of a computer data bus 43, which is under program control so that the desired signals may be generated by setting the control coefficients. The magnitude of the in phase component and the quadrature component of the measurable signal at output 23 is communicated to a computer input bus 44 via a multiplexer 45 and an analogue to digital converter 46 (ADC). A latch 47 controlled by the computer output bus 43 selects either the in phase component output line 37 or the quadrature output line 38 for onward communication via the ADC 46. The rate of communication may be chosen in accordance with the known principles governing sampling of analogue signals. Additionally a latch 47 is provided for other control functions, such as control of the rotatable probe for crack detection on control lines 52. The output of the computer bus 43 is also receivable at a video interface 48 for onward transmission to a visual display unit so that a visual display of results and operation may be provided. The control function of the data bus output 43 is achieved whenever the relevant enable input is signalled from a computer output port in accordance with the following table.

ENABLE 1: Set amplitude of balance signal quadrature component.
ENABLE 2: Set amplitude of balance signal in phase component.
ENABLE 3: Set Frequency Control—Excitation Generator.
ENABLE 4: Set Amplitude Control.
ENABLE 5: Set Latch—control function.
ENABLE 6: Set Latch—Multiplexer control.
ENABLE 7: Data to Video Interface.

An opposing coil 49 of the rotatable probe may be switched in place of the balance signal generator by indexing the switch 50 so that the probe may be positioned directly over the rivet. If the probe is not correctly positioned an error signal will be produced as the probe is rotated due to the asymmetry and the probe movement required for centering may be computed.

Figure 1:
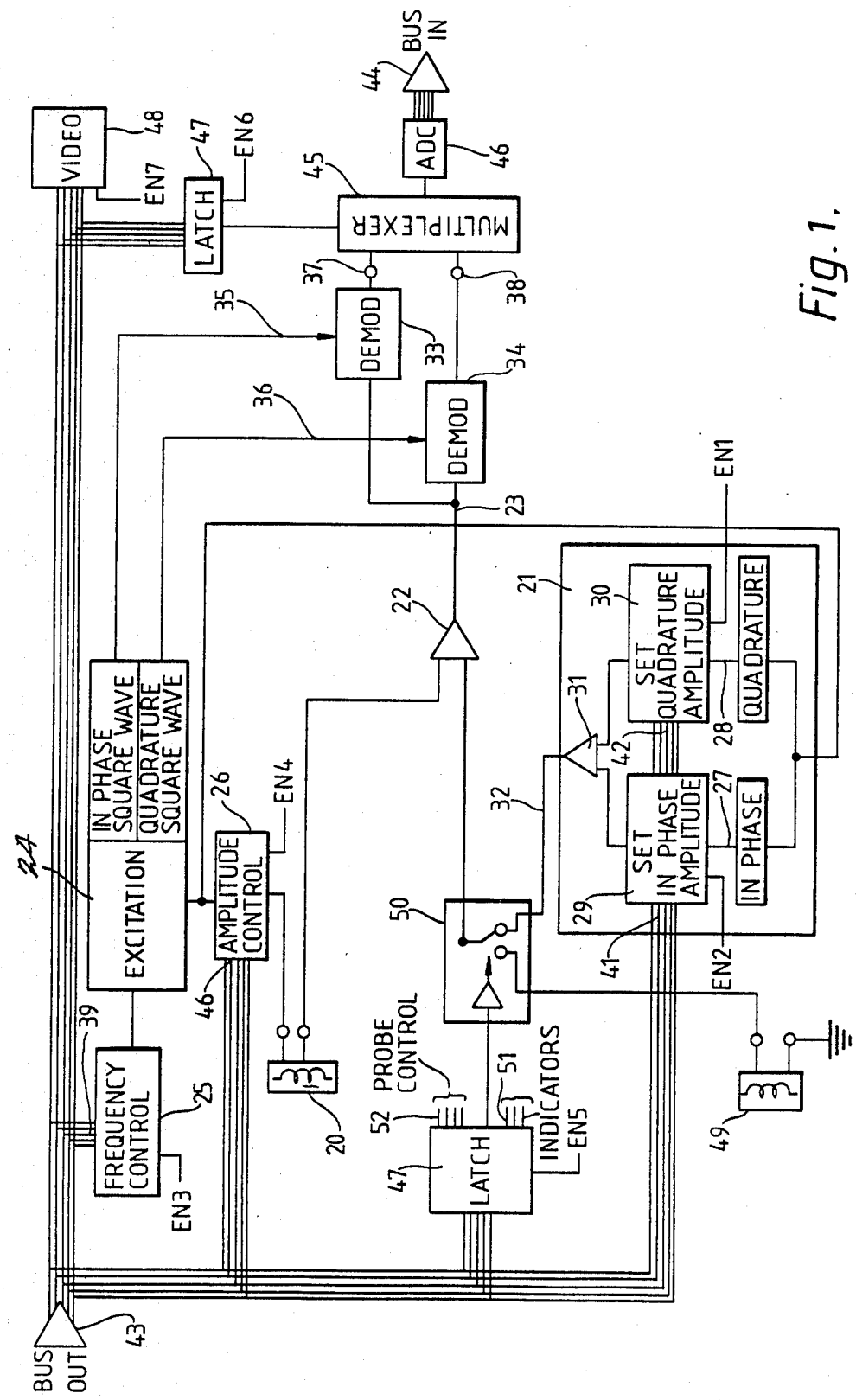
FIG. 1 represents an embodiment of the present invention.
Figure 2:
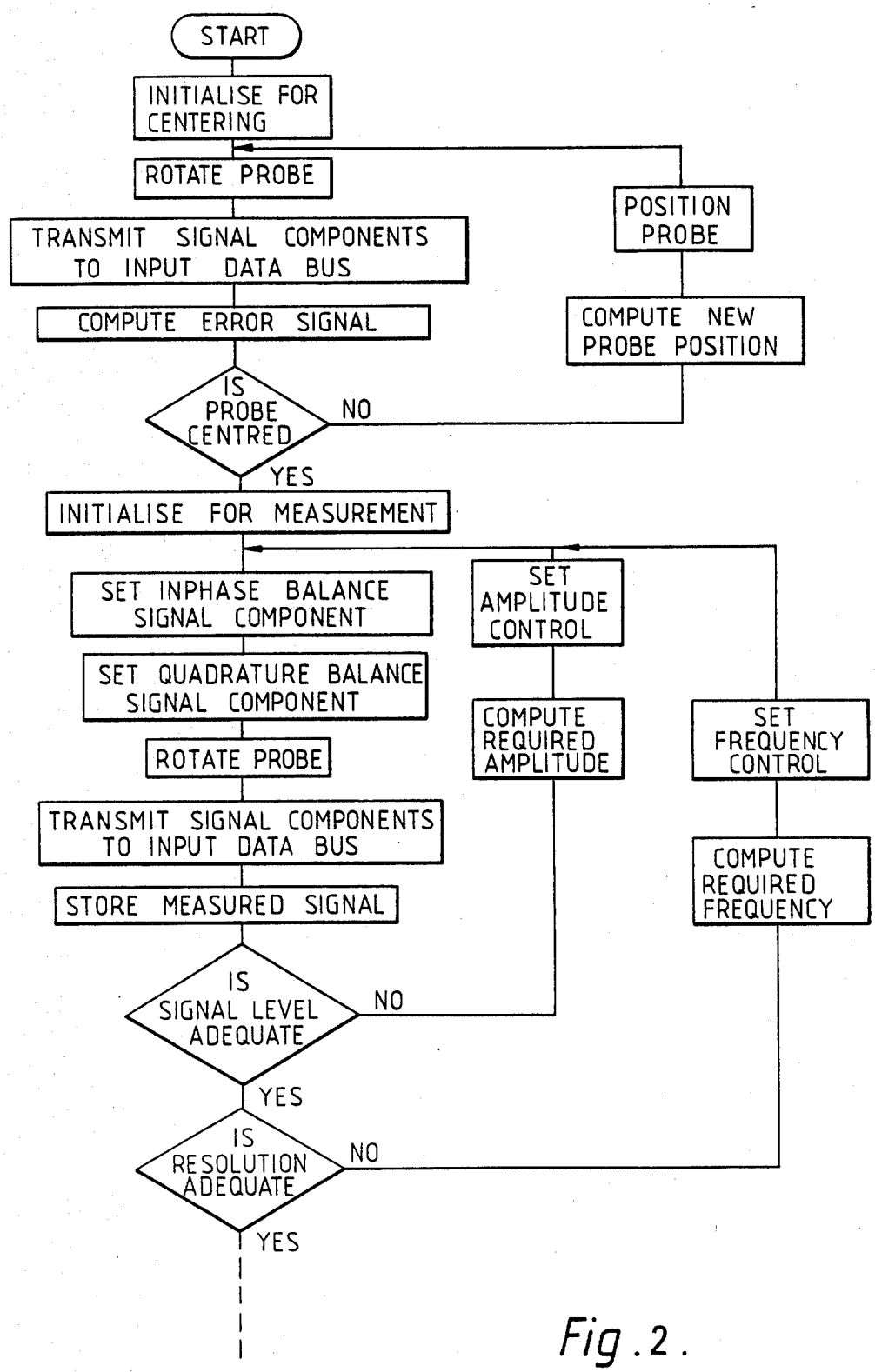
FIG. 2 and FIG. 2 (continued) represent, in flow chart form, the operation of the embodiment of FIG. 1.
Figure 2:
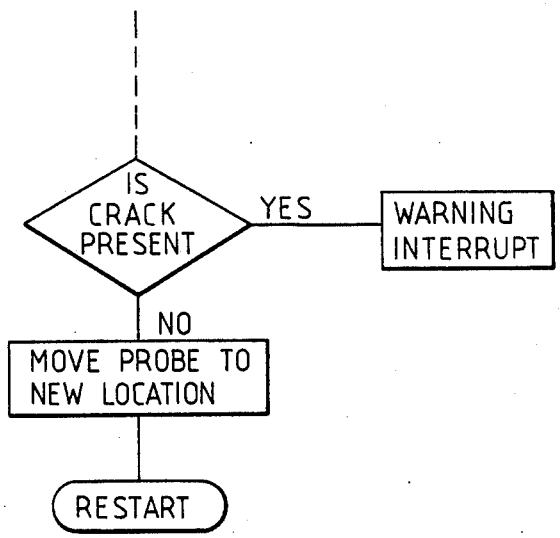

The operation of the apparatus may be controlled under computer control via the computer output bus 43. The measurable signal produced may be received in component form in digital format at the computer input bus 46 for subsequent interpretation and presentation. The operation may, for example, be made iterative in accordance with a program conforming to the flow chart of FIG. 2.

The control coefficients are initially set to estimated values based on previous measurements or calculations. The centring of the probe is determined by monitoring the signal at output 23 with the opposing coil 49 switched in circuit by switch 50 indexed by the latch 47. If the probe is inaccurately centered a new location for the probe may be computed and the probe moved. The probe may advantageously be moved by an operator on the basis of signals generated by the computer on indicator lines 51. The time taken for the centering operation may be reduced by providing additional input circuitry for coil pairs disposed oppositely on the same circumference as the coil pair 20 and 29.

In accordance with the present invention the signal from the coil 20 is balanced by setting the control coefficients of the in phase component amplitude control 29 and the quadrature component amplitude control 30 to produce a measurable signal at output 23. A measurement is made by rotation of the coil 20 as hereinbefore described. The in phase and quadrature components of the signal are transmitted to the computer input bus 44 for storage. The received signal may be analysed to establish suitability, in terms of signal level (amplitude) and resolution (frequency) for a decision on the presence of a crack to be made. If the decision level of confidence is inadequate the control coefficients of the frequency control 25 and the amplitude control 26 may be set iteratively until a decision may be made with the required level of confidence.

The program may advantageously be arranged to facilitate a plurality of subsequent measurements and to issue a warning interrupt only if the presence of a crack is detected. Status reports and a visual display of the position and magnitude of cracks may be provided visually via the video interface 48.

I claim:

1. An eddy current measurement apparatus for non-destructive testing in the vicinity of a fastener, comprising:
 a probe having first and second transducer coils structurally mounted in opposition on a rotatable former, said transducer coils providing output signals in response to excitation;
 means for exciting said coils;
 means for rotating said probe;
 difference amplifier means having first and second inputs and an output providing a first signal for measurement during rotation of said coils and a second signal indicating a centering error signal during rotation of said coils,
 said output of said first transducer coil being connected to said first input of said difference amplifier means;
 a signal generator providing a reference level signal;
 switch means having a first state and a second state arranged such that in said first state said second transducer coil output is connected to said second input of said difference amplifier means and such that in said second state said output of said signal generator is connected to said second input and said second transducer coil is disconnected from said second input;

control means for actuating said switch means into said first state during probe centering rotation so that said difference amplifier produces said center erroring signal and for actuating said switch means into said second state during a subsequent measurement;

said control means being arranged to repeat said centering rotation if said centering error signal at the output of said difference amplifier means indicates a centering error.

2. Measurement apparatus as claimed in claim 1 and wherein said signal generator provides a signal having a first component at substantially an in-phase component of said reference level and a second component at substantially a quadrature component of the reference level.

* * * * *